United States Patent
Kelley

(10) Patent No.: US 10,145,833 B2
(45) Date of Patent: Dec. 4, 2018

(54) DETECTION METHOD

(75) Inventor: Joan Kelley, Guilford (GB)

(73) Assignee: CONIDIA BIOSCIENCE LIMITED (GB)

( * ) Notice: Subject to any disclaimer, the term of this patent is extended or adjusted under 35 U.S.C. 154(b) by 851 days.

(21) Appl. No.: 10/468,691

(22) PCT Filed: Feb. 21, 2002

(86) PCT No.: PCT/GB02/00747
§ 371 (c)(1),
(2), (4) Date: Jan. 24, 2004

(87) PCT Pub. No.: WO02/068959
PCT Pub. Date: Sep. 6, 2002

(65) Prior Publication Data
US 2004/0115748 A1    Jun. 17, 2004

(30) Foreign Application Priority Data
Feb. 23, 2001   (GB) .................................... 0104566

(51) Int. Cl.
*G01N 33/22*   (2006.01)
*G01N 33/569*   (2006.01)

(52) U.S. Cl.
CPC ....... *G01N 33/22* (2013.01); *G01N 33/56961* (2013.01)

(58) Field of Classification Search
USPC ....... 435/203, 68.1, 395, 201, 69.1; 427/154
See application file for complete search history.

(56) References Cited

U.S. PATENT DOCUMENTS 5,658,747 A * 8/1997 Feldsine et al. ............. 435/7.32
5,665,585 A * 9/1997 Torkkeli et al. ............. 435/203
6,139,775 A   10/2000 Thames ........................ 252/328

FOREIGN PATENT DOCUMENTS

WO   WO 00/53699   9/2000

OTHER PUBLICATIONS

The Conidia Bioscience Fuelstat(TM) resinae (Aviation) Diagnostic Kit. (C) ConidiaBioscience 2000-2003.*
Taxonomic Details, species: Amorphotheca resinae. In, New Zealand Fungi. (C) Landcare Research 2001-2004.*
Lopes, P.T.C. 1996. Use of Immunofluorescence to detect the fungus Hormoconis resinae in aviation kerosine. International Biodeterioration & Biodegradation 37: 37-40.*
Greenspan et al. (Nature Biotechnology 17: 936-937, 1999).*
Lopes et al. (International Biodeterioation and Biodegradation vol. 37, pp. 37-40, 1996).*
Sheridan et al. (Tuatara: vol. 19, Issue 3, 1972, pp. 130-165).*
Kwak et al. (Journal of Microbiology and Biotechnology vol. 9, No. 6, pp. 764-772).*
Brigmon, RL, Franck, MM, Bray, JS, Scott, DF, Lanclos, KD, and Fliermans, CB, "Direct immunofluorescence and enzyme-linked immunosorbent assays for evaluating organic contaminant degrading bacteria," Journal of Microbiological Methods, 32: 1-10, 1998.
Gaylarde, CC, Bento, FM, and Kelley, J, "Microbial Contamination of Stored Hydrocarbon Fuels and its Control," Revista de Microbiologia, 30: 1-10, 1999.
Lopes, PTC and Gaylarde, C, "Use of Immunofluorescence to Detect the Fungus Hormoconis resinae in Aviation Kerosine," International Biodeterioration & Biodegradation, 37:37-40, 1996.

* cited by examiner

*Primary Examiner* — Robert A Zeman
(74) *Attorney, Agent, or Firm* — McCarter & English, LLP

(57) ABSTRACT

A method of analysis of a hydrocarbon fuel for the presence of a micro-organism comprises contacting a fuel sample with an aqueous diluent and with an antibody reactive with the micro-organism, or reactive with a metabolite or breakdown product produced by the micro-organism, to detect the presence or absence of the micro-organism.

12 Claims, No Drawings

DETECTION METHOD

The present invention relates to a method for analysis of hydrocarbon fuel.

It is known that hydrocarbon fuel can become contaminated with micro-organisms, which is undesirable. For example, *Hormoconis resinae* (the 'Jet Fuel Fungus') can grow on aviation kerosene causing corrosion and blockage problems in aircraft wing tanks. Airlines are required to send samples to laboratories for testing if contamination is suspected. Most laboratories use standard culture techniques which can take up to ten days to confirm. There are so-called "rapid" tests on the market. All, however, are based on culture techniques which take 72 hours for a result to be obtained.

Most airlines cannot accept even this delay, and automatically use a biocide: tests are therefore merely retrospective confirmation of a problem. A genuinely rapid test method would remove the expense of downtime and biocide treatments which are actually unnecessary.

At present there is still no rapid test available for the presence of micro-organisms in hydrocarbon fuel. The present invention sets out to address this problem.

In a first aspect, the present invention relates to a method of analysis of a liquid hydrocarbon fuel for the presence of a micro-organism, the method comprising contacting a fuel sample with an antibody reactive with the micro-organism, or reactive with a metabolite or breakdown product produced by the micro-organism, to detect the presence or absence of the micro-organism.

The method suitably comprises the steps of mixing a sample of the hydrocarbon fuel and an antibody reactive with the micro-organism of interest, followed by detection of the binding of the antibody with the micro-organism.

It has been found that the treatment of fuel with an antibody raised against a micro-organism provides a very rapid assay for the presence of that micro-organism in the fuel. By way of example, tests for *Hormoconis resinae* in aviation fuel have been developed which produce results in 90 minutes. In this way, the present invention allows biocides to be used only when needed, which is desirable as biocides are potentially dangerous compounds to use and handle. In contrast, Campos Lopes and Gaylarde, Int. Biodeterioration & Biodegradation (1996) 37-40, disclose a method in which the fuel sample is filtered and the filter pad is then blocked, dried, fixed with formaldehyde, washed three times incubated with specific antibody and washed again three times. Antibody conjugate is then added and further incubated. After three washings the filter is dried and observed, the entire process taking over four hours.

Any liquid hydrocarbon fuel may be analysed for micro-organism contamination using the present invention, although suitably the analysis is carried out on light-middle distillate fuel. Preferred are liquid fuels and fuel components having a boiling point below 390° C., such as aviation and diesel fuel, and hydrocarbon fuels with equivalent or similar composition. Other suitable-hydrocarbon fuels are well known in the art. Gasoline is another preferred fuel in the present invention.

The invention relates to the detection of any micro-organism that may be present in hydrocarbon fuel. For example, bacteria, yeasts and fungal species may all be analysed using the method of the invention. Examples of bacteria which can live in hydrocarbon fuel, and for which analysis is preferred include *Pseudomonas* and *Alcaligenes* species, with preferred examples of yeasts including Candida, Yarrowia and Rhodotorula species, although the invention is not limited to analysis of these species alone. Particularly preferred is the fungal species *Hormoconis resinae*, also known as *Cladosporium resinae*, and called *Amorphotheca resinae* during its sexual stage. Other fungi include *Aspergillus fumigatus, A. niger, Alternaria alternata, Paecilomyces viriotii* and *Pencillium* sp.

The term 'antibody', as used herein, relates to any suitable immunological agent which is reactive with a particular micro-organism. The term 'antibody' is thus not limited simply to naturally occurring antibodies, and includes fragments of whole antibodies and antibodies derivatives, for example. If antibody fragments or derivatives are used, we prefer that the reactivity of the agent to the antigen of the micro-organism is substantially maintained as compared with the whole native antibody, such that the antibody can be used to detect the micro-organism. Both monoclonal and polyclonal antibodies may be used in the present invention, and preparation of such antibodies is standard in the art.

At the molecular level, it will be appreciated that antibody reactivity or specificity is generally determined by antigens expressed or associated with a micro-organism. Accordingly any reference to antibody reactivity for a micro-organism herein generally refers to this antibody-antigen interaction, which defines the antibody target and specificity.

The presence of a micro-organism in hydrocarbon fuel may also be indicated by the presence of metabolites or breakdown products of the micro-organism of interest. Antibodies raised to such metabolites or breakdown products also allow detection of micro-organisms in hydrocarbon fuel, and use of such antibodies is also covered by the present invention.

Preferably the antibody is specific to the micro-organism of interest, or reactive with metabolites and/or breakdown products specific to the micro-organism of interest. In this way, a particular species of micro-organism may be identified using the invention. However, it is also possible to use an antibody in the present invention which is reactive with an antigen or derivative common to a number of species. In this case, the antibody is not species-specific, but still allows detection of a class of micro-organism present in the hydrocarbon fuel. Accordingly, the present invention also relates to a method for detection of a class of micro-organism in the hydrocarbon fuel, the class being defined by a common antigen.

Depending upon the assay and detection methods used, antibodies for use in the present invention may optionally be conjugated to other proteins or chemical markers, to facilitate detection of the antibody binding to antigen. Preferred are antibodies conjugated to enzymatic elements such as alkaline phosphatase, or readily detectable groups such as colloidal gold, biotin and streptavidin. Other suitable conjugation agents are well known in the art.

Any suitable detection method may be used in the present invention for analysis of antibody binding. Preferred are methods in which the result is detected optically or visually, such as colorimetric assays. Suitably an ELISA assay may be used, such as a sandwich or double layer assay, methods for which are standard in the art. Preferred is a competition assay in which antigen attached to a substrate, such as a microtitre dish, and antigen in the test sample compete for antibody binding.

Detection of antibody binding may also be carried out using lateral flow devices, such as dipsticks, which are again standard in the art. Pregnancy kits available on the market illustrate a simple embodiment of such technology. By way of example, a test sample of antigen can be applied to a dipstick, the dipstick comprising a suitable wick and an immobilised antibody reactive with the antigen. The wicking movement of the sample along the dipstick brings any antigen into contact with the immobilised antibody. Bound antigen can then be detected, for example, by further reaction with a labelled antibody. Other embodiments of dipstick technology and analysis methods using such technology are standard in the art.

Whilst radiolabelled detection systems are less preferred, nevertheless, methods involving radiolabelling (such as radioimmunoassay and radioallergosorbent testing) are also effective in the detection of antibody-antigen binding of the present invention.

In a particularly preferred embodiment of the invention, the method of analysis comprises contacting the fuel and antibody in the presence of an emulsifier. The presence of an emulsifier facilitates the interaction between the antibody and antigen in the fuel sample.

Any suitable emulsifier can be used in the invention. Preferred are strong emulsifiers and emulsifiers which minimise any denaturing effect of alkanes in the fuel sample on the antibody. Emulsifier suitability may be readily assessed, for example, by comparing antibody binding to antigen in a contaminated fuel sample in the presence of different emulsifiers.

Non-ionic surfactants are generally preferred in the present invention, with alkyl-ethoxylate surfactants such as Tritons and polyoxyethylene sorbitan monoesters such as polyoxyethylene (20) sorbitan monolaurate (also known as Tween 20) particularly preferred as emulsifiers. Suitably, an emulsifier such as Tween 20 may be prepared in deionised water, and used at a concentration of 0.01-10%, preferably 1-5%, most preferably 2.5% by volume. However, optimum concentrations of emulsifiers are likely to vary with the fuel being analysed, and can be readily ascertained by the person skilled in the art.

The method of the present invention does not require culturing of the micro-organism, and thus results can thus be obtained very rapidly. Typically the method provides a result in less than 2 hours from the start of the fuel analysis, i.e. the point at which the fuel sample is first treated in any way.

The invention further relates to kits for use in the analysis of the present invention. Preferably, a kit for use in the invention comprises a sample of antigen derived from a micro-organism capable of growing in liquid hydrocarbon fuel, an antibody reactive with that antigen, and a suitable emulsifier, as described above.

Optionally, the kits of the present invention comprise one or more additional components selected from the following list: suitable substrates pre-coated with the antigen or the antibody (such as microtitre dishes), suitable antigen standards, labelling reagents to label the antibody reactive with the micro-organism, further (detection) antibodies which are reactive with the first (micro-organism specific) antibody, detection reagents such as ELISA substrate reagents, stop solutions and wash solutions.

The present invention further relates to methods for the preparation of a micro-organism and suitable antigens for use in the present invention, comprising a step of incubation of the micro-organism in liquid hydrocarbon fuel for at least one step of the growth process. The micro-organism and/or antigen is then suitably recovered from the growth media using standard techniques. In this way, the configuration of antigens present in and on a micro-organism, and the configuration of metabolites and derivatives derived therefrom, are likely to mirror those present in the samples derived from hydrocarbon fuel. In this way, the antibody reaction against antigens in test samples of fuel may be optimised.

Accordingly the invention also relates to antibodies generated to micro-organisms grown in liquid hydrocarbon fuel and antibodies to metabolites or derivatives of micro-organisms grown in fuel oil, such antibodies optionally comprising a label for detection. The invention also relates to methods and kits for the analysis of a liquid hydrocarbon fuel as described herein utilising such antibodies.

The present invention is now illustrated by, but not limited to, the following Example.

EXAMPLE 1

Analysis of *H. resinae* in Hydrocarbon Fuel Using ELISA

Materials

Antigen/*Hormoconis resinae* Preparation

The antigen preparation is used in both the coating of the microplates and production of the standards used in the ELISA test.

1 *H. resinae* is grown on malt extract agar (toffee barley malt extract 20 g, agar oxoid no. 3 20 g, 1 liter of tap water, pH 6.5, autoclaved at 121° C. for 15 minutes) for 7-10 days at 25° C.

2 A spore suspension is prepared in 'Bushnell Haas' (Difco) liquid broth. Approximately 3 mls suspension per 100 mls fuel preparation are used as an inoculant as described below.

3 *H. resinae* is inoculated into in a fuel medium prepared by floating sterile susceptible fuel over sterile Bushnell Haas broth in the approximate ratio of 1:3.

4 The medium is incubated at 25° C. until a confluent fungal mat is obtained in the vessel.

5 The mat is filter harvested from the medium and washed in sterile distilled water.

6 The mat is then homogenised in sterile distilled water over ice in a Mickle bead beater for 4 minutes.

7 The resulting suspension is spun in a centrifuge (5 mins@5000 rpm) and washed three times in sterile distilled water.

8 The final homogenate pellet is freeze dried and this product is used as the antigen.

Antigen for Plate Coating

1 A 2 mg/ml solution of homogenised antigen was prepared in PBS buffer pH 7.4 and vigorously shaken overnight at 4° C.

2 20 µg/ml of the antigen suspension is then made up in TRIS Buffer (50 mM Tris) at pH 8.5 and coated onto the wells of microtitre plates at 100 µl/well.

3 The plates are then incubated overnight at 4° C.

4 The plates are washed with a blocking/glazing buffer which contains 5% by weight lactose, 0.2% by weight fish gelatin and 0.1% sodium azide made up in deionised water (the blocking is due to the presence of the fish gelatin protein and the glazing is due to the presence of lactose).

5 The plates are incubated for 1 hour at room temperature before liquid is aspirated and plates left to dry at ambient temperature overnight.

Antigen for Plate Standards

PBS buffer with 20% ethanol is added to a volume (of known concentration e.g. 2 mg/ml) of the antigen suspension to produce standards of appropriate concentration e.g. suitably 100 µg/ml, 30 µg/ml, 5 µg/ml.

Antibody

The antigen prepared from *H. resinae* (above) was used to generate a polyclonal antibody in sheep using standard techniques.

Conjugate Reagent (Tracer)

A Donkey anti-sheep antibody conjugated to Alkaline Phosphatase conjugate was used as a tracer in the assay, to identify the sheep anti-*H. resinae* antibody. It is also possible to conjugate the alkaline phosphatase protein to the sheep anti-*H. resinae* polyclonal antiserum, and then use it directly as a tracer in the assay.

Sample Diluent

The sample diluent comprises 2.5% by volume Tween 20, prepared in deionised water.

Assay Reagents for an ELISA Method (May Be Provided as a Kit)

1 *Hormoconis resinae* pre-coated microplate 12×8 strips (suitably provided in a sealed bag).
2 *Hormoconis resinae* standards: Standard concentrations range between 0-100 μg/ml. Each vial labelled with concentration.
3 *Hormoconis resinae* antibody in Tris buffer with inert blue dye (cresyl Blue at 15 mg/liter), protein stabiliser (BSA 1% w/v) and sodium azide 0.1% w/v.
4 Donkey anti-sheep second labelled antibody Reagent: In Tris buffer with inert blue dye and protein stabiliser (as above) and sodium azide 0.1% w/v.
5 ELISA substrate reagent: Consists of phenophthalein monophosphate (PMP, made up at 22.5 g/2.5 liters) and an enzyme co-factor ($MgCl_2$ 1M/2.5 liters) in diethanolamine buffer (262.5 g/2.5 liters, made up in deionised water).
6 ELISA stop solution: Consists of sodium hydroxide (70 g/liter) and a chelating agent (EDTA, 74.4 g/liter) in a diethanolamine buffer as above.
7 ELISA wash buffer concentrate (×10 Conc). Consists of phosphate buffer (PBS pH 7.4) with sodium azide, 0.1% w/v final concentration and Tween (0.5% v/v final concentration).

Materials and Equipment Required

Precision pipettors and disposable tips.
Microtitre plate reader with 550 nm filter.
Microtitre plate washer.
Distilled or Deionised water.
Microtitre plate shaker.

Method

Sample Preparation

1 Thoroughly mix the fuel sample.
2 Aliquot the fuel sample(s) from the container and add an equal amount of sample diluent. The test can be used to assess water and/or fuel phases.
3 Mix vigorously for a few seconds to emulsify.
4 Take 100 μl of the mixture and add as instructed in the Assay protocol (below).

Assay Protocol

1. Remove the pre-coated plate from the sealed bag and record sample and control locations on a 12×8 template sheet.
2. Pipette 100 μl of the standards and samples into the appropriate wells. Standards should be run in duplicate. Each sample should also be run in duplicate for optimum results.
3. Dispense 50 μl *Hormoconis resinae* antibody to each well. Cover the plate and incubate at room temperature (20-25° C.) for 30 minutes using the plate shaker.
4. Wash the plate 4 times with ELISA wash buffer as above (300 μl/well), invert and tap firmly on absorbent paper. Ensure the wells are quite dry.
5. Dispense 100 μl donkey anti-sheep alkaline phosphatase conjugate antibody to each well. Cover the plate and incubate at room temperature (20-25° C.) for 30 minutes using a plate shaker.
6. Wash the plate 4 times with wash buffer as above (300 μl/well), invert and tap firmly on absorbent paper. Ensure the wells are quite dry.
7. Dispense 100 μl of ELISA Substrate Reagent as above to each well. Cover the plate and incubate at room temperature (20-25° C.) for 30 minutes using the plate shaker.
8. Dispense 50 μl ELISA Stop Solution as above to each well. Mix by gently tapping the side of the plate.
9. Wipe the under surface of the plate free of condensation with a soft tissue. Read the plate using a Microtitre Plate Reader at 550 nm.

EXAMPLE 2

Analysis of Fuel Sample

Fuel samples were supplied by an airline for testing. 2 samples were known to have fungal contamination as tested by conventional culture assays. Samples were treated as outlined in Example 1. Samples were emulsified and run on the day of the assay. Results are shown below. The results of the ELISA assay confirm the culture assay, with samples 2082/32 and /36 having high fungal content.

| Samples Identity | Conc. ug/ml | Conc. ug/100 ml |
| --- | --- | --- |
| 2082/32 | >200 | >20000 |
| 2082/33 | 1 | 100 |
| 2082/34 | 0.30 | 30 |
| 2082/35 | 0.34 | 34 |
| 2082/36 | 134 | 13400 |
| 2082/37 | 1.8 | 180 |
| 2082/38 | 0.4 | 40 |
| 2082/39 | 0 | 0 |

The invention claimed is:

1. A method of analysis of a sample of a liquid hydrocarbon fuel for the presence of *Hormoconis resinae*, the method comprising the steps of:
   1) mixing the liquid fuel sample with an aqueous diluent containing an emulsifier;
   2) contacting the mixture or one phase thereof with an antiserum comprising antibodies raised against a homogenized preparation of *Hormoconis resinae*, wherein the *Hormoconis resinae* in the homogenized preparation was grown in contact with the liquid hydrocarbon fuel; and
   3) detecting the presence or absence of bound antibodies in the sample,
   wherein the method provides a result within two hours from step 1, and wherein the detection of bound antibodies indicates the presence of *Hormoconis resinae* which is actively growing in liquid hydrocarbon fuel.

2. The method of claim 1, wherein the method comprises vigorously mixing the sample of fuel and the aqueous diluent before contacting the mixture with the antibodies.

3. The method of claim 1, wherein the emulsifier is a non-ionic detergent.

4. The method of claim 3, wherein the emulsifier is polyoxyethylene (20) sorbitan monolaurate.

5. The method of claim 4, wherein the emulsifier is used at a concentration of from 1 to 10% by volume.

6. The method of claim 1, wherein the hydrocarbon fuel is light-middle distillate fuel having a boiling point below 390° C.

7. The method of claim 1, wherein the fuel sample is not filtered prior to the step of contacting the mixture or one phase thereof with the antibodies.

8. The method of claim 1, wherein the antibodies are not incubated with a filter used to filter the sample of the liquid hydrocarbon fuel.

9. A kit for analyzing a sample of a liquid hydrocarbon fuel for the presence of *Hormoconis resinae*, the kit comprising:
   1) a homogenized preparation of *Hormoconis resinae*, wherein the *Hormoconis resinae* in the homogenized preparation was grown in contact with liquid hydrocarbon fuel;
   2) an antiserum comprising antibodies raised against a homogenized preparation of *Hormoconis resinae*, wherein the *Hormoconis resinae* in the homogenized preparation was grown in contact with the liquid hydrocarbon fuel; and
   3) an aqueous diluent containing an emulsifier.

10. The kit of claim 9, further including a substrate to which the antibodies are immobilized.

11. The kit of claim 10, wherein the substrate is a microtiter plate.

12. The kit of claim 9, further including a lateral flow device to which the antibodies are immobilized.

* * * * *